(12) United States Patent
Oikawa et al.

(10) Patent No.: US 10,321,894 B2
(45) Date of Patent: Jun. 18, 2019

(54) SPECIMEN INFORMATION ACQUISITION APPARATUS

(75) Inventors: Katsuya Oikawa, Tokyo (JP); Makoto Yamakawa, Kyoto (JP); Tsuyoshi Shiina, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 395 days.

(21) Appl. No.: 14/119,411

(22) PCT Filed: May 11, 2012

(86) PCT No.: PCT/JP2012/062728
§ 371 (c)(1),
(2), (4) Date: Mar. 17, 2014

(87) PCT Pub. No.: WO2012/161103
PCT Pub. Date: Nov. 29, 2012

(65) Prior Publication Data
US 2014/0206995 A1    Jul. 24, 2014

(30) Foreign Application Priority Data
May 26, 2011    (JP) .................................. 2011-118095

(51) Int. Cl.
*A61B 8/08* (2006.01)
*A61B 8/00* (2006.01)
*G01S 7/52* (2006.01)

(52) U.S. Cl.
CPC ............ *A61B 8/485* (2013.01); *A61B 8/0825* (2013.01); *A61B 8/403* (2013.01); *A61B 8/429* (2013.01); *A61B 8/4227* (2013.01); *A61B 8/5223* (2013.01); *A61B 8/54* (2013.01); *G01S 7/52042* (2013.01); *A61B 8/0858* (2013.01)

(58) Field of Classification Search
None
See application file for complete search history.

(56) References Cited

U.S. PATENT DOCUMENTS

| 5,810,731 | A | * | 9/1998 | Sarvazyan | ........... A61B 5/0048 600/438 |
| 6,770,033 | B1 | * | 8/2004 | Fink | ......................... A61B 8/08 600/443 |
| 2010/0160778 | A1 | | 6/2010 | Eskandari et al. | |

(Continued)

FOREIGN PATENT DOCUMENTS

| CN | 1838913 A | 9/2006 |
| CN | 101856243 A | 10/2010 |

(Continued)

*Primary Examiner* — Bo Joseph Peng
(74) *Attorney, Agent, or Firm* — Canon USA Inc., IP Division

(57) ABSTRACT

The present invention relates to formation of an image indicating viscoelastic characteristics in a specimen by a simple method.
Stepwise pressurization in which, after pressure is instantaneously increased to a certain pressure value, the certain pressure value is kept for a certain time period is performed to measure the variation with time of strain distribution in the specimen and to calculate a stress from strain distribution at a saturation measurement time when the effect of the viscosity of a viscoelasticity measurement reference layer is saturated, thereby evaluating the modulus of elasticity and the coefficient of viscosity of a body tissue.

13 Claims, 6 Drawing Sheets

(56) References Cited

U.S. PATENT DOCUMENTS

2011/0040185 A1* 2/2011 Matsumura .............. A61B 8/00
600/443
2017/0215847 A1* 8/2017 Oikawa ................. A61B 8/485

FOREIGN PATENT DOCUMENTS

| EP | 2078495 A1 | 7/2009 |
| EP | 2272435 A1 | 1/2011 |
| JP | 2005066041 A | 3/2005 |
| JP | 2007222605 A | 9/2007 |

* cited by examiner

SPECIMEN INFORMATION ACQUISITION APPARATUS

TECHNICAL FIELD

The present invention relates to specimen information acquisition apparatuses and, more particularly, to a specimen information acquisition apparatus that make pictures of viscoelastic characteristics of a specimen.

BACKGROUND ART

Ultrasonic diagnostic apparatuses are known as the specimen information acquisition apparatuses. Since the ultrasonic diagnostic apparatuses non-invasively make pictures indicating information in specimens to acquire the pictures, the ultrasonic diagnostic apparatuses are widely used in medical fields.

For example, ultrasonic tomographic images and ultrasonic Doppler images have heretofore been used in the ultrasonic diagnostic apparatuses. The ultrasonic tomographic images result from imaging of the inner structures of living bodies from reflection echo caused by the difference in reflectivity between tissues and the ultrasonic Doppler images result from imaging of blood flow speeds or the likes by using the Doppler effect of ultrasonic waves caused by blood flows.

In addition, the hardness of tissues measured by using ultrasonic waves is recently started to be used for tissue diagnosis. This is because the hardness of tissues is deeply related to pathological states. For example, it is known that sclerosis cancers including breast cancers and thyroid cancers are likely to be sclerotic, compared with normal tissues and benign tumors.

Furthermore, it is reported in recent years that cancers differ from benign tumors in their viscosity characteristics in mammary tumors. Viscoelastic characteristics including the viscosity characteristics are required to be evaluated, in addition to the measurement of the hardness of tissues, in the tissue diagnosis. Accordingly, in addition to the measurement of the distributions of the viscoelastic characteristics in living bodies by using the ultrasonic waves, pictures of the distributions of the viscoelastic characteristics in the living bodies and pictures of the structures of tissues in related art are required to be used in combination in the diagnosis of cancers of tissue regions and so on.

PTL 1 discloses an ultrasonic diagnostic apparatus that calculates the viscosity of a specimen. In the ultrasonic diagnostic apparatus in PTL 1, an ultrasonic probe including a pressure sensor provided on a surface of a transducer that transmits and receives ultrasonic waves is used to measure the strain distribution by using the ultrasonic waves and also measure the distribution of pressure to be applied on the specimen with the pressure sensor in order to calculate the values of the elasticity and the viscosity from the strain distribution and the pressure distribution. Since the distribution of the pressure that has been actually applied is measured, in addition to the measurement of the strain distribution, in the above configuration, it is possible to realize the distribution measurement with high accuracy without uniformly applying the pressure.

PTL 2 discloses an ultrasonic diagnostic apparatus as a pressure measurement method. In the ultrasonic diagnostic apparatus in PTL 2, a deformation part for measurement the modulus of elasticity of which is known is sandwiched between an ultrasonic probe and a body tissue to measure the pressure. Specifically, the deformation in the deformation part for measurement is measured by using the ultrasonic waves and the pressure (stress) applied on the deformation part for measurement is calculated from the relationship between the modulus of elasticity and the strain to calculate the distribution of the modulus of elasticity in the specimen from the stress and the strain distribution in the specimen and display the calculated distribution of the modulus of elasticity.

However, the structure of the ultrasonic probe is complicated in the configuration described in PTL 1. In addition, there is a problem in that, when the strain distribution of tissues is measured by using the ultrasonic waves, it is difficult to measure the strain distribution of tissues with a normal pressure sensor because the pressure (stress) to be applied is normally very small. Furthermore, there is a problem in that, when the pressure sensor is provided immediately below the ultrasonic probe, it is not possible to perform the measurement for deep regions because the efficiency and the sensitivity of transmission and reception of the ultrasonic waves are degraded.

The ultrasonic diagnostic apparatus in PTL 2 is simple in the configuration. However, only the elasticity distribution in a specimen is displayed and a method of measuring the viscosity distribution in the specimen is not disclosed in PTL 2. Accordingly, there is a need for an apparatus capable of calculating the viscosity of a specimen with a simple configuration.

CITATION LIST

Patent Literature

PTL 1 Japanese Patent Laid-Open No. 2007-222605
PTL 2 Japanese Patent Laid-Open No. 2005-66041

SUMMARY OF INVENTION

The present invention provides a specimen information acquisition apparatus that transmits elastic waves to a specimen and receives the elastic waves reflected in the specimen to acquire information in the specimen. The specimen information acquisition apparatus includes a conversion element configured to convert the received elastic waves into an electrical signal; a reference layer provided between the conversion element and the specimen, a modulus of elasticity of the reference layer being known; a measurement unit configured to measure a strain in the specimen and a strain of the reference layer when pressure is applied on the specimen and the reference layer by using the electrical signal; and a calculation unit configured to calculate a coefficient of viscosity of the specimen by using the modulus of elasticity of the reference layer, a variation in the strain in the specimen, and a saturation value of the strain of the reference layer.

Advantageous Effects of Invention

According to the present invention, the specimen information acquisition apparatus is capable of evaluating the modulus of elasticity and the coefficient of viscosity of a body tissue with a simple configuration. In particular, the present invention provides the specimen information acquisition apparatus that is effectively used for diagnosis of a tumor tissue because of independent calculation of the modulus of elasticity and the coefficient of viscosity of a specimen.

DESCRIPTION OF EMBODIMENTS

Embodiments of the present invention will herein be described in detail with reference to the attached drawings.

Figure 1:
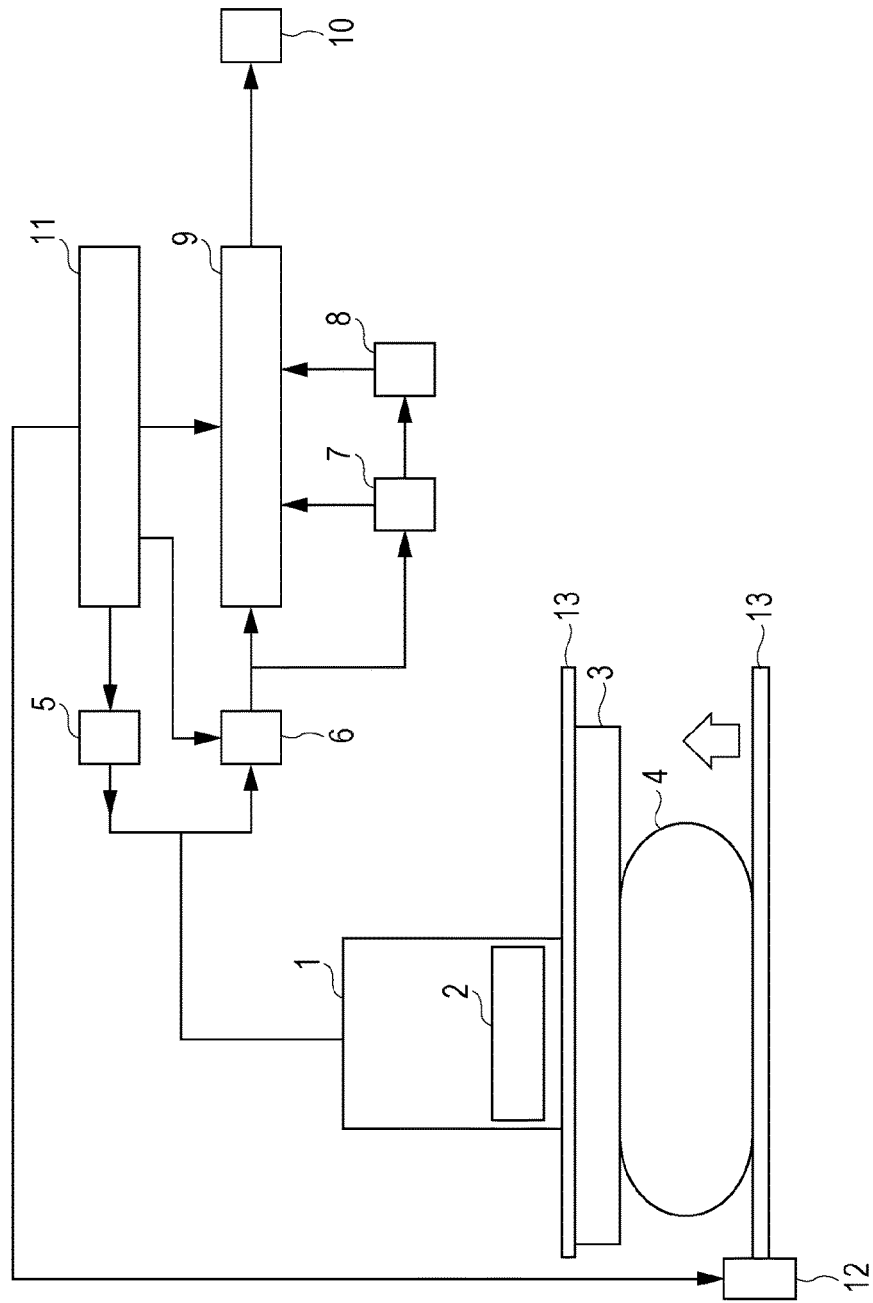
FIG. 1 is a block diagram showing an example of the configuration of an ultrasonic diagnostic apparatus according to an embodiment of the present invention.

FIG. 1 is a block diagram showing an example of the configuration of an ultrasonic diagnostic apparatus, which is a specimen information acquisition apparatus according to an embodiment.

The ultrasonic diagnostic apparatus uses ultrasonic waves to display a tomographic image of a region to be diagnosed in a specimen and an image based on the viscoelasticity of a body tissue, particularly, based on the coefficient-of-viscosity distribution thereof, in addition to the modulus-of-elasticity distribution thereof.

The ultrasonic diagnostic apparatus shown in the example in FIG. 1 includes a pair of compression plates that holds and compress a specimen and applies pressure on the specimen in a stepwise manner via the compression plates. The application of pressure in a stepwise manner is hereinafter referred to as stepwise pressurization. Holing the specimen and applying the pressure on the specimen by using the compression plates allows stress that is temporally constant to be applied on the specimen and a viscoelasticity measurement reference layer before a saturation measurement time during the stepwise pressurization. In addition, it is possible to stably measure the strain distribution in multiple scanning processes using the ultrasonic waves.

Referring FIG. 1, the ultrasonic diagnostic apparatus includes a probe 1 including a transducer array 2. The transducer array 2 is a conversion element serving as both a unit that transmits the ultrasonic waves, which are elastic waves, to a specimen 4 described below and a unit that receives the ultrasonic waves, which are elastic waves, reflected from the specimen to convert the ultrasonic waves into an electrical signal. A viscoelasticity measurement reference layer 3 the modulus of elasticity (Ec) of which is known is provided between the transducer array 2 and the specimen 4. In the example in FIG. 1 in the present embodiment, the viscoelasticity measurement reference layer 3 is provided between one of a pair of compression plates 13 for compressing the specimen 4, described below, and the specimen 4. The ultrasonic diagnostic apparatus in FIG. 1 also includes a transmission unit 5 that transmits a control signal to the probe 1 and a reception unit 6 that receives the electrical signal supplied from the conversion element in the probe 1. The ultrasonic diagnostic apparatus further includes a strain distribution detecting unit 7, which is a measurement unit that uses the electrical signal supplied from the conversion element in the probe 1 to measure the strain in the specimen 4 and the strain of the viscoelasticity measurement reference layer 3, which occur when pressure is applied on the specimen 4 and the viscoelasticity measurement reference layer 3. The ultrasonic diagnostic apparatus further includes a viscoelasticity distribution calculating unit 8, which is a calculation unit that uses the variation in the measured strain in the specimen 4, a saturation value of the strain of the viscoelasticity measurement reference layer 3, and the known modulus of elasticity of the viscoelasticity measurement reference layer 3 to calculate the coefficient of viscosity of the specimen 4. The ultrasonic diagnostic apparatus in FIG. 1 can include an imaging unit 9, a display unit 10, a control unit 11, the pair of compression plates 13 for compressing the specimen 4, and a pressure driving unit 12 that controls the compression pressure applied on the specimen 4 by the compression plates 13. The principle of calculating the coefficient of viscosity of the specimen 4 with the ultrasonic diagnostic apparatus will now be described.

In the present embodiment, the stepwise pressurization is performed in which, after the pressure applied on the specimen 4 from the probe 1 is instantaneously increased to a certain pressure value manually or in a mechanically driven manner, the certain pressure value is held for a certain time period. The ultrasonic waves, which are elastic waves, are concurrently transmitted from the probe 1 to the specimen 4 via the viscoelasticity measurement reference layer 3 the modulus of elasticity of which is known to measure the strain distribution of the viscoelasticity measurement reference layer 3 and the strain distribution in the specimen 4.

The strain occurring in a tissue in the specimen during the application of the pressure is calculated according to (Equation 1) when the tissue has no viscosity:

[Math. 1]

$$\varepsilon = \frac{\sigma_0}{E} \qquad \text{(Equation 1)}$$

In (Equation 1), E denotes an elastic constant (Young's modulus) of the tissue and $\sigma_0$ denotes the amplitude of a stress (pressure) applied in the stepwise manner. When the tissue has no viscosity, the elasticity of the tissue is calculated from the amplitude value of the strain. When the viscoelasticity measurement reference layer 3 has no viscosity, the stress is calculated from the amount of strain.

Figure 2:
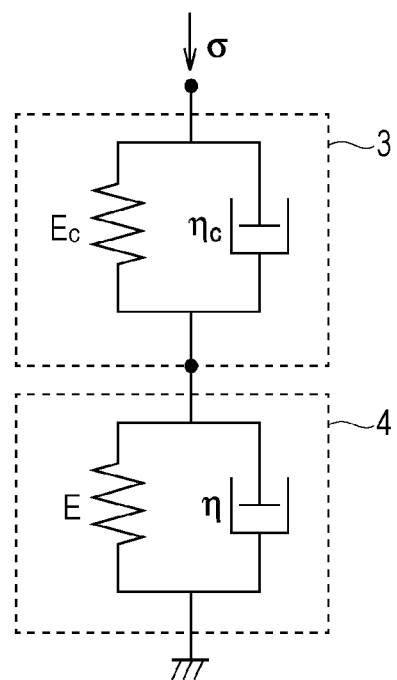
FIG. 2 shows the principle of measurement of viscoelasticity.

In contrast, when the tissue has a viscosity, the strain is analyzed by using a dynamic model for viscoelasticity measurement shown in FIG. 2. Referring to FIG. 2, reference numeral 3 denotes the viscoelasticity measurement reference layer and reference numeral 4 denotes an area in the specimen. Ec denotes the Young's modulus (modulus of elasticity) of the viscoelasticity measurement reference layer 3, ηc denotes the coefficient of viscosity of the viscoelasticity measurement reference layer 3, E denotes the Young's modulus (modulus of elasticity) of the specimen 4, and η denotes the coefficient of viscosity of the specimen 4.

Since the specimen 4 and the viscoelasticity measurement reference layer 3 are independently varied with time on the basis of the respective viscoelasticities, it is necessary to perform the measurement in accordance with the dynamic model shown in FIG. 2. In particular, when the viscoelasticity measurement reference layer 3 is formed of a member that is excellent in ultrasonic wave propagation characteristics and that has acoustic characteristics similar to those of the tissue of the specimen to suppress the reflection from the boundary face between the viscoelasticity measurement reference layer 3 and the specimen 4, discarding the viscosity of the viscoelasticity measurement reference layer 3 can cause an large error in practical measurement. Accordingly, it is difficult to independently calculate the stress only from the Young's modulus of the viscoelasticity measurement reference layer 3.

Figure 3:
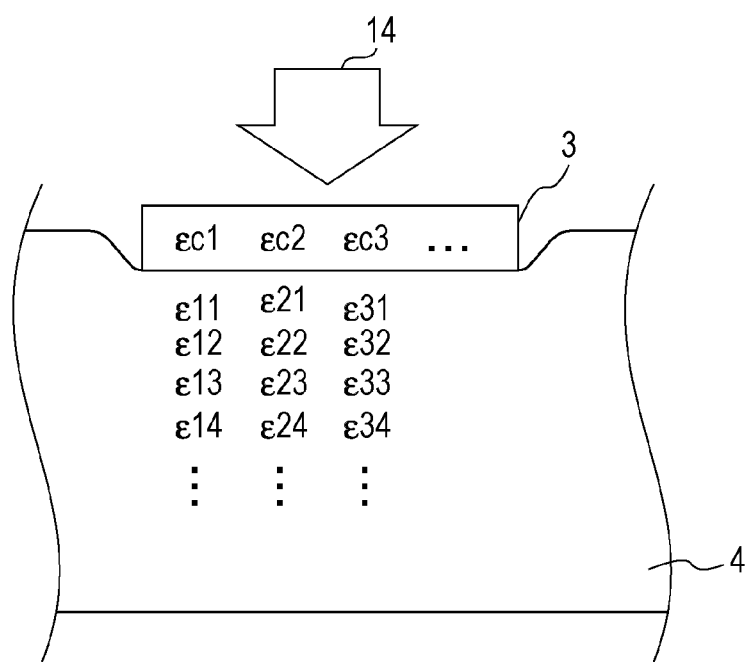
FIG. 3 is a diagram for describing measurement of viscoelastic distribution according to an embodiment.

The relationship between a variation with time σ(t) of the stress, a variation with time εc(t) of the strain of the viscoelasticity measurement reference layer 3, and a variation with time ε(t) of the strain in the specimen 4 in accordance with a dynamic model shown in FIG. 3 is as follows:

[Math. 2]

$$\sigma(t) = E_c \varepsilon_c(t) + \eta_c \frac{d\varepsilon_c(t)}{dt} \qquad \text{(Equation 2)}$$

[Math. 3]

$$\sigma(t) = E\varepsilon(t) + \eta \frac{d\varepsilon(t)}{dt} \qquad \text{(Equation 3)}$$

In the present embodiment, the stepwise pressurization is performed in which, after the pressure applied on the specimen 4 from the probe 1 is instantaneously increased to a certain pressure value manually or in a mechanically driven manner, the certain pressure value is held for a certain time period.

In the dynamic model shown in FIG. 3, the variation with time εc(t) of the strain of the viscoelasticity measurement reference layer 3 and the variation with time ε(t) of the strain in the specimen 4 are as follows:

[Math. 4]

$$\varepsilon_c(t) = \frac{\sigma_0}{E_c} - \left(\frac{\sigma_0}{E_c} - \varepsilon_c^{(0)}\right) e^{-\frac{t}{\tau_c}} \qquad \text{(Equation 4)}$$

[Math. 5]

$$\varepsilon(t) = \frac{\sigma_0}{E} - \left(\frac{\sigma_0}{E} - \varepsilon^{(0)}\right) e^{-\frac{t}{\tau}} \qquad \text{(Equation 5)}$$

However, τc=ηc/Ec and τ=η/E. In addition, $\varepsilon^{(0)}$ and $\varepsilon_c(0)$ denote the value (initial value) of the strain in the specimen 4 and the value (initial value) of the strain of the viscoelasticity measurement reference layer 3, respectively, at the moment when the stepwise pressurization is performed. Since the strains in the specimen 4 and the viscoelasticity measurement reference layer 3 are equal to zero at the moment when the pressure is applied, (Equation 4) and (Equation 5) are modified to the following equations:

[Math. 6]

$$\varepsilon_c(t) = \frac{\sigma_0}{E_c}\left(1 - e^{-\frac{t}{\tau_c}}\right) \qquad \text{(Equation 4')}$$

[Math. 7]

$$\varepsilon(t) = \frac{\sigma_0}{E}\left(1 - e^{-\frac{t}{\tau}}\right) \qquad \text{(Equation 5')}$$

The variation with time of the strains of the viscoelasticity measurement reference layer 3 and the strain in the specimen 4 can be followed in the above manner to calculate the respective time constants τc and τ. However, it is difficult to independently calculate the Young's moduli and the coefficients of viscosity of the viscoelasticity measurement reference layer 3 and in the specimen 4 from the respective time constants. Accordingly, the values of at least the Young's modulus and the coefficient of viscosity of the viscoelasticity measurement reference layer 3 are required to be known. In addition, when the stress $\sigma_0$ is unknown, it is necessary to perform complicated calculation in order to simultaneously solve (Equation 4') and (Equation 5').

When a time t after the start of the stepwise pressurization is sufficiently long, the strain of the viscoelasticity measurement reference layer 3 is substantially constant as follows:

[Math. 8]

$$\varepsilon_c \cong \frac{\sigma_0}{E_c} \qquad \text{(Equation 6)}$$

Accordingly, it is possible to calculate the stress $\sigma_0$ from the value of the strain of the viscoelasticity measurement reference layer 3 measured at the time t by using the known Young's modulus. In particular, the above expression is established regardless of whether the strain of the viscoelasticity measurement reference layer 3 at the start of the stepwise pressurization has a value of zero.

The time when the stress $\sigma_0$ is measured according to (Equation 6) is hereinafter referred to as the saturation measurement time. It is sufficient for the saturation measurement time to be several times of τc. For example, the calculation accuracy of the stress $\sigma_0$ is 1% or lower when the saturation measurement time is five times of τc and the calculation accuracy of the stress $\sigma_0$ is about 0.1% when the saturation measurement time is nine times of τc. Accordingly, when the approximate magnitude of the coefficient of viscosity of the viscoelasticity measurement reference layer 3 is known, the approximate value of τc can be calculated to determine the saturation measurement time. Since it is sufficient for the saturation measurement time to be several times of τc, it is sufficient to acquire the approximate value of the coefficient of viscosity of the viscoelasticity measurement reference layer 3. In addition, when the coefficient of viscosity of the viscoelasticity measurement reference layer 3 is unknown, the variation with time of the strain of the viscoelasticity measurement reference layer 3 may be measured with the stepwise pressurization being performed to the viscoelasticity measurement reference layer 3 in advance and the time when the variation with time is made constant within the range of the measurement accuracy may be measured to experimentally determine the saturation measurement time.

The value at the time when the strain in the specimen 4 is made constant may be used, instead of the value at the time when the strain of the viscoelasticity measurement reference layer 3 is made constant, in the calculation of the stress $\sigma_0$. However, since the time constant $\tau$ of the specimen 4 is varied depending on the tissue to be measured and the saturation measurement time is also varied depending on the specimen 4, it is difficult to determine the saturation measurement time. Accordingly, the value of the strain of the viscoelasticity measurement reference layer 3 is desirably used.

As described above, in the present embodiment, it is possible to measure the stress from the strain of the viscoelasticity measurement reference layer 3 measured at the saturation measurement time by the simple calculation. In addition, the present embodiment has the advantage in that it is sufficient for the viscoelasticity measurement reference layer 3 to be made of a material the Young's modulus of which is known. The Young's modulus can be measured relatively accurately and stably, compared with the coefficient of viscosity or the like.

Then, the ratio $\tau$ between the coefficient of viscosity and the Young's modulus is calculated from the variation in the strain in the specimen measured at the start of the stepwise pressurization.

Specifically, the logarithm of the differentiation with respect to time of the strain in the specimen 4 is calculated as follows:

[Math. 9]

$$\ln\left[\frac{d}{dt}\varepsilon'(t)\right] = -\frac{t}{\tau} + \ln\left(\frac{\sigma_0}{\tau E}\right) \quad \text{(Equation 7)}$$

The logarithm of the differentiation with respect to time of the strains in the specimen 4 at different time points is used to calculate the reciprocal of the ratio $\tau$ between the coefficient of viscosity and the Young's modulus, which represents the slope. In addition, the intercept is calculated from the following expression:

[Math. 10]

$$\ln\left(\frac{\sigma_0}{\tau E}\right)$$

The Young's modulus E of the specimen is calculated from the intercept, the stress $\sigma_0$ calculated according to (Equation 6), and the ratio $\tau$ between the coefficient of viscosity and the Young's modulus. Then, the ratio $\tau$ and the Young's modulus E are used to calculate the coefficient of viscosity.

Although the strain in the specimen at the moment when the stepwise pressurization is started is set to zero, the intercept is represented in the following manner from (Equation 5) when the specimen originally has the strain $\varepsilon^{(0)}$:

[Math. 11]

$$\ln\left(\frac{\sigma_0}{\tau E} - \frac{\varepsilon^{(0)}}{\tau}\right)$$

Since the ratio $\tau$ is calculated in the above manner, the intercept may be corrected with the following value when the detected initial strain $\varepsilon^{(0)}$ exists:

[Math. 12]

$$\frac{\varepsilon^{(0)}}{\tau}$$

It is hereinafter assumed that the intercept when the initial strain exists is corrected in the above manner.

Alternatively, (Equation 5') may be directly subjected to fitting to calculate the ratio $\tau$ between the coefficient of viscosity and the Young's modulus and a reference strain coefficient $\sigma_0/E$ and, then, the Young's modulus E of the specimen may be calculated from the reference strain coefficient $\sigma_0/E$ and the stress $\sigma_0$ calculated according to (Equation 6). Least square may be used for the fitting. When the specimen has the initial strain, (Equation 5) may be subjected to the fitting by using the initial strain $\varepsilon^{(0)}$.

Since the variation in the strain in the specimen 4 is larger at the start of the stepwise pressurization and is easy to be measured, the measurement of the strain in the specimen 4 is desirably started immediately after the start of the stepwise pressurization. Since it is sufficient to calculate the slope and the intercept with respect to time of the logarithm of the differentiation with respect to time of the strain in the specimen 4 for the calculation using (Equation 7), it is sufficient to measure the strain in the specimen 4 at several to several tens of time points after the start of the stepwise pressurization. The measurement may not be continued until the saturation measurement time of the strain in the specimen 4.

Specifically, the strain in the specimen 4 is measured by transmission and reception of the ultrasonic waves, which are elastic waves, at relatively short time intervals from the time when the stepwise pressurization is started to calculate the slope and the intercept with respect to time of the logarithm of the differentiation with respect to time of the strain in the specimen 4. Then, the transmission and reception of the ultrasonic waves and the measurement of the strain are stopped, the strain of the viscoelasticity measurement reference layer 3 is measured by transmission and reception of the ultrasonic waves after the saturation measurement time is reached, and the stress $\sigma_0$ is calculated to calculate the Young's modulus and the coefficient of viscosity in the specimen 4 from the slope and the intercept.

Also when (Equation 5') is directly subjected to the fitting, it is sufficient to detect the ratio $\tau$ between the coefficient of viscosity and the Young's modulus by using only the initial time points when the strain is largely varied with time and the measurement of the strain by transmission and reception of the ultrasonic waves may be subsequently stopped.

How to apply the measurement of the Young's modulus and the coefficient of viscosity described above to measurement of viscoelastic distribution in the specimen 4 will now be described with reference to FIG. 3. Referring to FIG. 3, reference numeral 3 denotes the viscoelasticity measurement reference layer, reference numeral 4 denotes the specimen, and reference numeral 14 denotes a force applied for the measurement. The force 14 is applied substantially vertical to the boundary face between the viscoelasticity measurement reference layer 3 and the specimen 4. The strains of the viscoelasticity measurement reference layer 3 and the tissue in the specimen 4 occur in the vertical direction in FIG. 3. The strain distribution of $\varepsilon c1$, $\varepsilon c2$, $\varepsilon c3$, . . . occurs along the boundary face between the viscoelasticity measurement reference layer 3 and the specimen 4 in the viscoelasticity measurement reference layer 3, the strain distribution of $\varepsilon 11$, $\varepsilon 12$, $\varepsilon 13$, . . . occurs in the vertical direction in the specimen 4, and the variation with time of these strain distributions is measured by using the ultrasonic waves. Since the force 14 is applied in the vertical direction in FIG. 3, the strain $\varepsilon c1$ of the viscoelasticity measurement reference layer 3 and the strains $\varepsilon 11$, $\varepsilon 12$, $\varepsilon 13$, . . . in the specimen 4, which are vertically aligned with each other, occur from the same stress. Similarly, the strain εci of the viscoelasticity measurement reference layer 3 and the strains εi1, εi2, εi3, . . . in the specimen 4 (i=2, 3, . . . ) occur from the same stress.

(Equation 7) is applied to the strains εi1, εi2, εi3, . . . (i=1, 2, 3, . . . ) in the specimen 4 with time from the time when the stepwise pressurization is started to calculate the ratio τ between the coefficient of viscosity and the Young's modulus and the intercept, as described above, or (Equation 5') is used to calculate the ratio τ between the coefficient of viscosity and the Young's modulus and the reference strain coefficient $\sigma_0/E$. Then, the stress at the position of the strain εci (i=1, 2, 3, . . . ) is calculated by using the strain εci (i=1, 2, 3, . . . ) of the viscoelasticity measurement reference layer 3, that is, the saturation value of the strain of the viscoelasticity measurement reference layer 3 at the time when the saturation measurement time is reached. The stress calculated here and the ratios τ and the intercepts (or the reference strain coefficients) at the positions of the strains εi1, εi2, εi3, . . . (i=1, 2, 3, . . . ) in the specimen 4, which are previously calculated, are used to calculate the Young's moduli and the coefficients of viscosity at the respective positions that are arranged vertically to the strain εci (i=1, 2, 3, . . . ) of the viscoelasticity measurement reference layer 3. The Young's moduli and the coefficients of viscosity at the respective positions in the specimen are calculated in the above manner to acquire the distribution of the Young's moduli and the distribution of the coefficients of viscosity.

On the basis of the above principle, the viscoelasticity measurement reference layer 3 the modulus of elasticity of which is known is provided between the transducer array 2, which is the conversion element that receives the elastic waves reflected from the specimen 4 to convert the elastic waves into the electrical signal, and the specimen 4, the strain in the specimen 4 and the strain of the viscoelasticity measurement reference layer 3 when the pressure is applied on the specimen 4 and the viscoelasticity measurement reference layer 3 are measured, and the coefficient of viscosity of the specimen 4 is calculated by using the variation in the strain in the specimen 4, the saturation value of the strain of the viscoelasticity measurement reference layer 3, and the modulus of elasticity of the viscoelasticity measurement reference layer 3. As described above, the control may be performed so that the stepwise pressurization in which, after the pressure applied on the specimen 4 and the viscoelasticity measurement reference layer 3 by the pressure driving unit 12 is instantaneously increased to a certain value, the certain value is held for a certain time period is realized. The pressure driving unit 12 is a pressure control unit that controls the pressure of the compression plates 13, which is a pressure applying unit applying the pressure on the specimen 4 and the viscoelasticity measurement reference layer 3.

In this case, as shown in FIG. 1 described above, it is desirable that the viscoelasticity measurement reference layer 3 be positioned on the side of one of the compression plates 13 opposing the specimen 4 so that the viscoelasticity measurement reference layer 3 is arranged between the specimen 4 and the compression plate 13 and that the transducer array 2, which is the conversion element, be positioned on the side opposite to the side of the compression plate 13 opposing the specimen 4 so that the transmission and reception of the ultrasonic waves to and from the specimen 4 are performed via the compression plate 13 and the viscoelasticity measurement reference layer 3.

Figure 4:
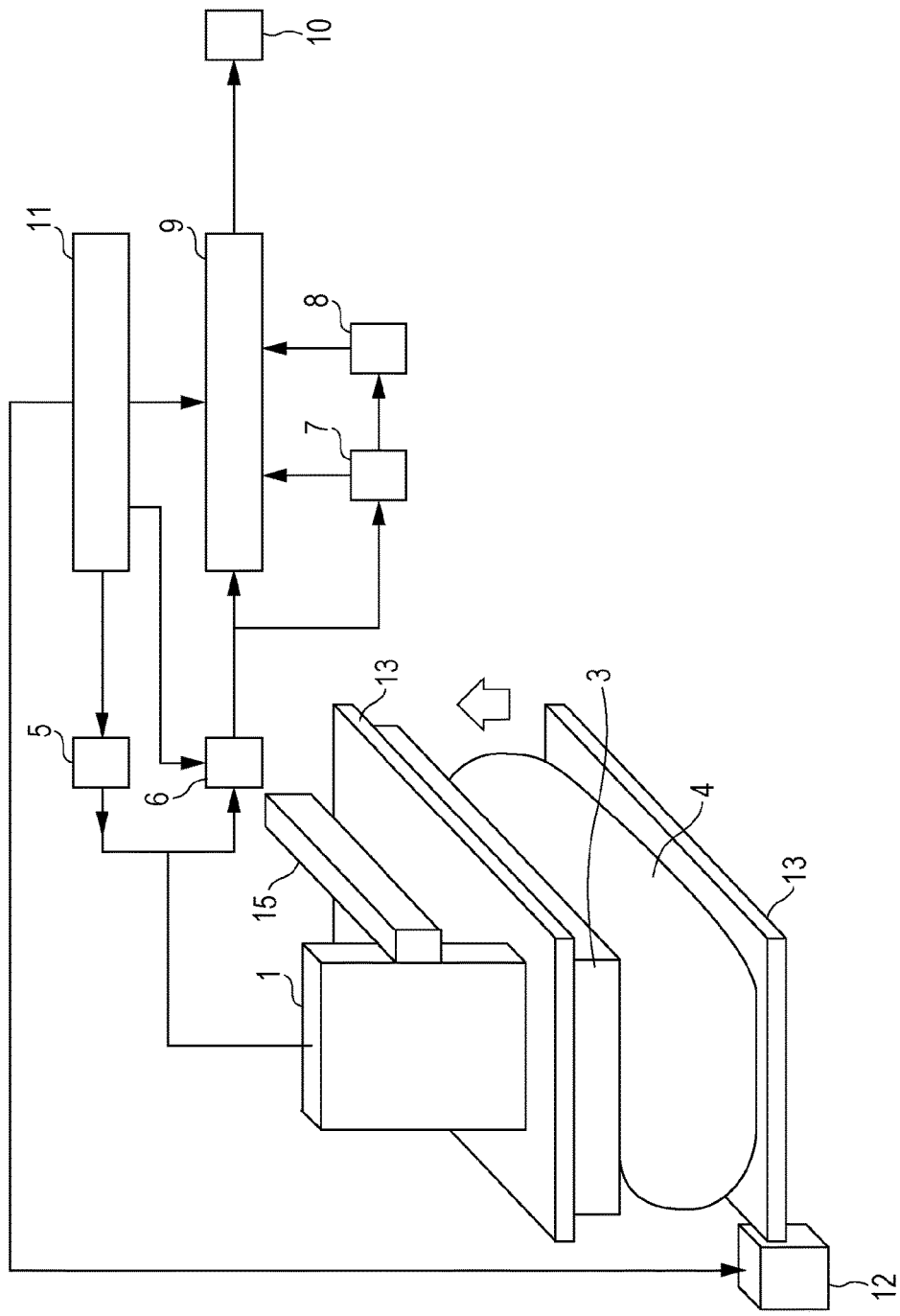
FIG. 4 is a block diagram showing an example of the configuration of an ultrasonic diagnostic apparatus according to a second embodiment.

In more specific and desirable strain measurement by using the ultrasonic waves, which are elastic waves, the scanning by using the ultrasonic waves may be performed in a manner shown in FIG. 4 described below to measure the strain distribution at each position in the specimen. Referring to FIG. 4, reference numeral 15 denotes a probe scanning unit. The scanning in the specimen 4 is repeated from the time when the stepwise pressurization is started with the probe scanning unit 15 to calculate the ratio τ between the coefficient of viscosity and the Young's modulus and the intercept (or the reference strain coefficient) at each point in the specimen 4 and, then, calculate the stress distribution at each point in the viscoelasticity measurement reference layer 3 by using the strain value of the viscoelasticity measurement reference layer 3 at the time when the saturation measurement time is reached, that is, the saturation value of the strain of the viscoelasticity measurement reference layer 3. Then, the Young's modulus and the coefficient of viscosity at each point in the specimen 4 are calculated by using the stress at each point of the viscoelasticity measurement reference layer 3 and the ratio τ and the intercept (or the reference strain coefficient) at each point in the specimen 4, which are vertically aligned with each other in FIG. 3.

As described above, the ultrasonic diagnostic apparatus in FIG. 4 further includes the probe scanning unit 15, which is a scanning unit that scans the transducer array 2, which is the conversion element. The control unit 11 controls the pressure so that the stepwise pressurization is performed in which the pressure applied on the specimen 4 and the viscoelasticity measurement reference layer 3 by the compression plates 13 is varied at the respective positions of the transducer array 2 to be scanned. The strain distribution detecting unit 7, which is the measurement unit, measures the strain distribution in the specimen 4 and the strain distribution of the viscoelasticity measurement reference layer 3 on the basis of the stepwise pressurization in which the pressure is varied. The viscoelasticity distribution calculating unit 8, which is the calculation unit, uses the modulus of elasticity of the viscoelasticity measurement reference layer 3, the strain distribution in the specimen 4, and the distribution of the saturation values of the strain of the viscoelasticity measurement reference layer 3 to calculate the coefficient-of-viscosity distribution of the specimen 4.

Figure 6A:
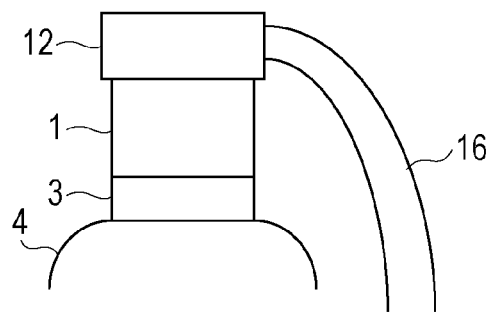
FIG. 6A shows an exemplary configuration indicating how a specimen is held.
Figure 6B:
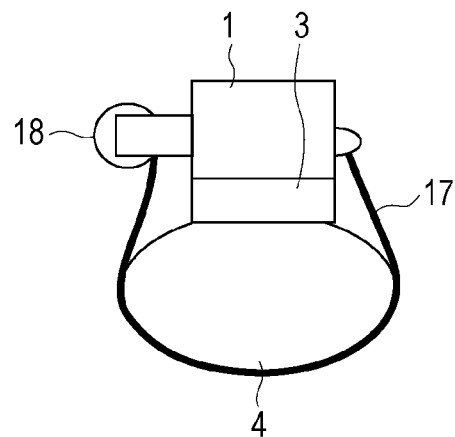
FIG. 6B shows another exemplary configuration indicating how the specimen is held.

The pressure applying unit applying the pressure on the specimen 4 and the viscoelasticity measurement reference layer 3 is not limited to the compression plates 13 described above. A tension band (belt) 17 that holds the specimen 4 may be used as the pressure applying unit, as shown in FIG. 6B described below. In this case, a binding unit 18 serving as the pressure control unit and the control unit 11 controlling the binding unit 18 control the tension of the tension band 17 to control the pressure to be applied on the specimen 4 and the viscoelasticity measurement reference layer 3.

Although the Young's modulus is used as the elasticity characteristic and the coefficient of viscosity is used as the viscosity characteristic, an elastic coefficient, such as a stiffness coefficient or a pressure-elasticity coefficient, and a viscosity coefficient, such as a degree of viscosity or a rate of viscosity, may be used.

First Embodiment

A first embodiment of the present invention will now be described with reference to the drawings. FIG. 1 is a block diagram showing an example of the configuration of an ultrasonic diagnostic apparatus according to the first embodiment, which is the specimen information acquisition apparatus. Components in the ultrasonic diagnostic apparatus will be sequentially described along with their operations.

[Holding of Specimen and Stepwise Pressurization]

The two compression plates 13 hold the specimen 4 and simultaneously perform the stepwise pressurization on the specimen 4 and the viscoelasticity measurement reference layer 3. The stepwise pressurization means pressurization in which, after the pressure applied on the specimen 4 and the viscoelasticity measurement reference layer 3 is instantaneously increased to a certain pressure value, the certain pressure value is held for a certain time period. Specifically, after the pressure driving unit 12 drives the compression plates 13 with the control unit 11 to instantaneously increase the pressure to a certain pressure value, the pressure driving unit 12 holds the certain pressure value for a certain time period for the stepwise pressurization. Alternatively, after the load between the two compression plates 13 with the specimen 4 sandwiched therebetween is controlled with the control unit 11 by using a measured load value from a load sensor (not shown) and the load is instantaneously increased to a certain load value, the certain load value may be held for a certain time period for the stepwise pressurization.

The pressurization by the pressure driving unit 12 causes non-uniform pressure distribution (stress distribution) on the boundary face between one of the compression plates 13 and the viscoelasticity measurement reference layer 3 depending on the shape and/or the hardness of the specimen 4. However, since the specimen 4 is held by the compression plates 13, the stress at each point in the specimen 4 is temporally constant during the stepwise pressurization under the control of the control unit 11. The viscoelasticity measurement reference layer 3 is provided on the side of one of the compression plates 13 opposing the specimen 4 so that the viscoelasticity measurement reference layer 3 is arranged between the compression plate 13 and the specimen 4. The probe 1 including the transducer array 2, which is the conversion element, is arranged on the side opposite to the side of the compression plate 13 opposing the specimen 4 to transmit and receive the ultrasonic waves to and from the specimen 4 via the compression plate 13 and the viscoelasticity measurement reference layer 3.

The compression plates 13 is desirably made of a material which is excellent in transmissivity of the ultrasonic waves, the reflection of the ultrasonic waves is difficult to occur between which and the viscoelasticity measurement reference layer 3 being in contact with one of the compression plates 13, and which has stiffness sufficient to hold the specimen 4, such as polymethylpentene polymer (registered trademark).

[Example of Specific Configuration of Viscoelasticity Measurement Reference Layer]

The viscoelasticity measurement reference layer 3 is arranged on the side of one of the compression plates 13, which are the pressure applying unit, toward the specimen 4. The stepwise pressurization is simultaneously performed to the viscoelasticity measurement reference layer 3 and the specimen 4 by the compression plates 13. The ultrasonic waves from the probe 1 are transmitted to and received from the specimen 4 via the viscoelasticity measurement reference layer 3.

The viscoelasticity measurement reference layer 3 is made of a material that propagates the ultrasonic waves and is not subjected to absorption and scattering and is desirably made of a material having firmness, flexibility, and appropriate elasticity. The propagation capability of the ultrasonic waves is important to transmit and receive the ultrasonic waves via the viscoelasticity measurement reference layer 3 for image formation and any attenuation occurring in the propagation of the ultrasonic waves due to the absorption or the scattering reduces the transmission and reception efficiency. Accordingly, the viscoelasticity measurement reference layer 3 is desirably made of a uniform material which is transparent to the ultrasonic waves, which has a small attenuation constant, and the propagation speed (sonic speed) of which is around the average sonic speed of the specimen 4. In addition, the difference in acoustic impedance between the viscoelasticity measurement reference layer 3 and the specimen 4 should not be large because the reflection occurs on the boundary face between the viscoelasticity measurement reference layer 3 and the specimen 4 to reduce the efficiency of the transmission and reception of the ultrasonic waves for the image formation if the difference in acoustic impedance between the viscoelasticity measurement reference layer 3 and the specimen 4 is large. However, since it is difficult to detect the boundary face described below if the acoustic impedance of the viscoelasticity measurement reference layer 3 coincides with that of the specimen 4, the viscoelasticity measurement reference layer 3 should have an appropriate difference in acoustic impedance with the specimen 4. Furthermore, since the pressure is applied on the specimen 4 via the viscoelasticity measurement reference layer 3 and the stress (pressure) distribution is measured by using the amount of deformation of the viscoelasticity measurement reference layer 3, the viscoelasticity measurement reference layer 3 desirably has the firmness, the flexibility, and appropriate elasticity. Although the material appropriate for the viscoelasticity measurement reference layer 3 is, for example, aqueous gel such as polyvinyl alcohol, polyurethane, or a rubber-based material, the viscoelasticity measurement reference layer 3 may be made of another material as long as the material has the above characteristics. However, the elastic coefficient, such as the Young's modulus, the stiffness coefficient, and the pressure-elasticity coefficient, of the material should be known. Although the viscoelasticity measurement reference layer 3 is desirably thin in terms of the propagation of the ultrasonic waves, the viscoelasticity measurement reference layer 3 is desirably subjected to appropriate deformation in order to measure the stress (pressure) distribution with high sensitivity and it is necessary for the viscoelasticity measurement reference layer 3 to be included in an area where the strain distribution is detected. Accordingly, the viscoelasticity measurement reference layer 3 has a thickness of 0.1 mm to 50 mm and preferably has a thickness of 1 mm to 10 mm.

[Generation of Reception Beam Signal and Display of B-Mode Image]

The probe 1 mechanically or electronically performs beam scanning to transmit and receive the ultrasonic waves to and from the specimen 4. The transducer array 2 includes transducers arranged therein, which are driven in response to a driving waveform from the transmission unit 5 to produce the ultrasonic waves. The transmission unit 5 produces the driving waveform to be supplied to each transducer in the transducer array 2 and simultaneously adjusts the timing when each transducer is driven under the control of the control unit 11. A combined ultrasonic wave resulting from combination of the ultrasonic waves produced in the individual transducers by adjusting the timing when the transducers are driven forms an ultrasonic wave transmission beam that converges into a certain point. In other words, the control unit 11 controls the transmission unit 5 to transmit the ultrasonic wave transmission beam that has a convergence point at a desired depth and that has directivity to a desired direction from the probe 1. The control unit 11 performs sector scanning in which the direction of the ultrasonic wave transmission beam is swung to perform the beam scanning. Alternatively, the control unit 11 performs linear scanning in which a limited number of transducers are driven in the transducer array 2 to create a transmission opening and the transmission opening is moved to perform the scanning in a substantially parallel manner with the ultrasonic wave transmission beam.

The reception unit 6 includes a reception circuit and a phasing addition circuit. The reception circuit converts the ultrasonic waves, which are elastic waves, received by each transducer in the transducer array 2 into an electrical signal (hereinafter sometimes referred to as a "reception signal"), amplifies each reception signal, and desirably performs analog-digital (AD) conversion to the reception signal to convert the reception signal into multiple time-series digital signals. The phasing addition circuit is used to form a reception beam based on the ultrasonic waves. Specifically, the phasing addition circuit adds a delay time controlled by the control unit 11 to each digitized reception signal to perform addition (phasing addition) to the digitized reception signal in order to generate a reception beam signal. The reception beam signal results from addition of the electrical signals (reception signals) the reception timing of which is adjusted and can be used to form an ultrasonic wave reception beam that has the directivity for the reception sensitivity and that has one or multiple convergence points. The reception signals result from conversion of the ultrasonic waves, which are elastic waves, received by the transducers. The control unit 11 performs the beam scanning to the reception beam based on the ultrasonic waves in synchronization with the ultrasonic wave transmission beam. As a result, the reception beam signal is generated, which results from transmission of the ultrasonic wave transmission beam from the probe 1 to the specimen 4 and reception of reflection echo signals of the ultrasonic waves, reflected from the tissue in the specimen 4, in the ultrasonic wave reception beam. The beam scanning by the control unit 11 generates multiple reception beam signals corresponding to the reflection echo signals of the ultrasonic waves at a specific position or in a specific direction in the specimen 4. Arranging the reception beam signals in association with the beam scanning generates a tomographic image corresponding to the reflection echo strength of the ultrasonic waves in the specimen 4. The beam scanning is repeated by the control unit 11 to generate the tomographic images at different points of time.

The multiple reception beam signals generated by the reception unit 6 are supplied to the imaging unit 9. The imaging unit 9 generates a monochromic B-mode tomographic image in which the tomographic structure in the specimen 4 is reflected from the multiple reception beam signals. The imaging unit 9 arranges the multiple reception beam signals in association with the beam scanning and performs signal processing, such as gain adjustment, filter processing, envelope detection, and/or log compression, to the multiple reception beam signals. In addition, the imaging unit 9 may include a digital scan conversion circuit that performs image processing, such as edge enhancement and/or image filtering, for image display after the signal processing to convert each reception beam signal into a display signal to be supplied to the display unit 10 and a digital-analog (DA) conversion circuit for conversion into an analog video signal. The display unit 10 is caused to display the B-mode tomographic image under the display control of the control unit 11.

The display unit 10 is a display apparatus, such as a cathode ray tube (CRT) or a liquid crystal display (LCD), and displays an image on the basis of the display signal supplied from the imaging unit 9.

[Example of Specific Configuration of Strain Distribution Detecting Unit]

The multiple reception beam signals generated by the reception unit 6 are also supplied to the strain distribution detecting unit 7, which is the measurement unit. The strain distribution detecting unit 7 detects the strain distribution in the specimen 4 and the strain distribution of the viscoelasticity measurement reference layer 3 on the basis of the multiple reception beam signals.

The strain distribution can be detected by performing correlation calculation between the reception beam signals at the same position, acquired on different beam scanning periods, as in a color flow Doppler method and a tissue tracking method that are common.

The strain distribution detecting unit 7 includes a memory circuit storing the multiple reception beam signals and a correlation calculation circuit.

The multiple reception beam signals resulting from repetition of the beam scanning by the control unit 11 are stored in the memory circuit. A set of reception beam signals acquired in a single beam scanning process composes frame reception beam signal data corresponding to the tomographic image at a certain point of time. Different pieces of frame reception beam signal data correspond to the beam scanning processes at different points of time. The reception beam signals at the corresponding position of the different pieces of frame reception beam signal data are the reflection echo signals of the ultrasonic waves from the same position in the beam scanning processes at different points of time. Accordingly, the correlation calculation between the reception beam signals can be performed to measure the displacement at the corresponding position occurring in the beam scanning processes at different points of time. The difference of the displacement distribution in the depth direction of the beam is calculated to detect the strain distribution.

The correlation calculation circuit includes a Hilbert transform filter at its input part, which converts the two reception beam signals corresponding to the same position in the beam scanning processes at different points of time into analysis signals to perform complex correlation calculation using the analysis signals. Alternatively, I-Q signals resulting from orthogonal detection of the reception beam signals may be used to calculate an instantaneous phase delay in time series between the two reception beam signals corresponding to the same position in the beam scanning processes at different points of time and the calculated instantaneous phase delay may be converted into the acoustic speed to find the displacement. In addition, the accuracy of the measurement of the strain may be improved by using complex autocorrelation or the like, which is popular in the art.

Examples of the specific configuration of the memory circuit and the correlation calculation circuit will now be described.

In a first example, the strain distribution detecting unit 7 includes the memory circuit storing the multiple pieces of frame reception beam signal data and multiple correlation calculation circuits corresponding to the individual beam positions in a single beam scanning process. Two pieces of frame reception beam signal data corresponding to the beam scanning processes at different points of time are selected from the multiple pieces of frame reception beam signal data stored in the memory circuit and the reception beam signals corresponding to the two pieces of frame reception beam signal data are supplied to the correlation calculation circuit corresponding to each beam position. Performing the correlation calculation in the correlation calculation circuits allows the displacement distribution in the depth direction of the beam at the corresponding beam position to be detected. In such a configuration, since the two pieces of frame reception beam signal data are selected from the multiple pieces of frame reception beam signal data acquired by repeating the beam scanning to perform the correlation calculation, it is possible to measure the displacement during the beam scanning processes at arbitrary two points of time. The difference of the strain in the depth direction is calculated to measure the amount of strain.

Although the multiple correlation calculation circuits performing one-dimensional correlation for every beam position are used in the above example, correlation calculation circuits performing two-dimensional correlation to the pieces of frame reception beam signal data in the beam scanning processes at different points of time may be used.

In a second example, the strain distribution detecting unit 7 includes multiple memory circuits and multiple correlation calculation circuits corresponding to the individual beam positions in the beam scanning. The multiple memory circuits include two First-In First-Out (FIFO) memories and a TMP memory temporarily storing the result of the correlation calculation. In the beam scanning that is repetitively performed, the reception beam signal at each individual beam position is first stored in a first FIFO memory. The output from the first FIFO memory is supplied to a second FIFO memory and the correlation calculation circuits, and the output from the second FIFO memory is supplied to the correlation calculation circuits. The two FIFO memories each have the memory capacity sufficient to store the reception beam signals acquired at the corresponding beam position in a single beam scanning process. Accordingly, at a certain point of time in the beam scanning repetitively performed, the two reception beam signals at the corresponding beam position in two successive beam scanning processes are stored in the FIFO memories, and the two reception beam signals are used to perform the calculation in the correlation calculation circuits in order to detect the displacement distribution in the depth direction of the beam at the corresponding beam position. The displacement distribution detected here occurs during the two successive beam scanning processes in the beam scanning repetitively performed. In order to calculate the displacement occurring during multiple beam scanning processes, the results in the correlation calculation circuits are accumulated. The result of the calculation in the correlation calculation circuits is added to the data in the TMP memory and the result of the addition is stored in the TMP memory. In addition, the difference of the displacement distribution in the depth direction is calculated to detect the strain distribution. This configuration is suitable for installation of the strain distribution detecting unit 7 in pipeline processing appropriate for real-time processing and the required capacity of the memory circuit is smaller than that in the first example.

In both the above examples, it is possible to detect the strain distribution in the depth direction of the beam occurring during different beam scanning processes from the multiple correlation calculation circuits corresponding to the individual beam positions. Arranging the strain distribution at the individual beam positions allows the strain distribution on a two-dimensional cross section occurring during different beam scanning processes to be detected.

In addition to the above two examples, the pieces of frame reception beam signal data acquired in the beam scanning processes at different points of time by a common method in the art may be used to detect the strain distribution on a two-dimensional cross section.

In the embodiments, the strain distribution is detected in an area including not only the specimen 4 but also the viscoelasticity measurement reference layer 3. More specifically, the area is set so that the amount of displacement in the boundary between the specimen 4 and the viscoelasticity measurement reference layer 3 is measured to detect the strain distribution of the viscoelasticity measurement reference layer 3. The amount of displacement in the viscoelasticity measurement reference layer 3 may be detected by cutting out the reception beam signals so as to include the reflection echo of the ultrasonic waves including that in the boundary to perform the series of correlation calculations. Alternatively, a calculation circuit described below may be separately provided in the strain distribution detecting unit 7.

Since the inner part of the viscoelasticity measurement reference layer 3 is generally substantially transparent to the ultrasonic waves, the reflection echo signal of the ultrasonic waves is very small and the reception beam signals are also small. Accordingly, the result of the correlation calculation of the reception beam signals in the above area can include an error to be unstable. In contrast, the reflection echo signal that is locally large is generated in the boundary between the specimen 4 and the viscoelasticity measurement reference layer 3 due to the difference in acoustic impedance between the specimen 4 and the viscoelasticity measurement reference layer 3 and, thus, the reception beam signals and the result of the correlation calculation of the reception beam signals can be detected with high accuracy. Since the viscoelasticity measurement reference layer 3 is made of a material that is uniform in its depth direction and the strain distribution in the depth direction of the viscoelasticity measurement reference layer 3 is also uniform, the strain distribution of the viscoelasticity measurement reference layer 3 can be detected by using the strain values calculated from the displacement in the boundary.

Accordingly, a threshold value circuit may be provided at the input part of the correlation calculation circuit and the reception beam signal the strength of which is lower than or equal to a predetermined value may be set to zero to perform the correlation calculation with a beginning part of each reception beam signal, that is, a part corresponding to the thickness of the viscoelasticity measurement reference layer 3 being masked, thereby removing the instability.

In addition, it may be determined that a part of the reception beam signal, the amplitude strength of which is lower than or equal to a predetermined value, is within the viscoelasticity measurement reference layer 3 to directly detect the boundary of the reception beam signals and to calculate the displacement in the boundary during different beam scanning processes from the difference between the pieces of frame reception beam signal data corresponding to the beam scanning processes in the boundary. The difference in the depth direction of the displacement distribution in the boundary between the specimen 4 and the viscoelasticity measurement reference layer 3 calculated in the above manner may be calculated to detect the strain distribution of the viscoelasticity measurement reference layer 3.

The amount of strain of the viscoelasticity measurement reference layer 3 is calculated from a part near the beginning of each reception beam signal and the strain distribution along the depth direction of the specimen 4 is calculated from the following part thereof in the above manner. Arranging the strain distribution at the beam position corresponding to each reception beam signal allows the strain distribution on the cross section of the specimen 4 and the strain distribution of the viscoelasticity measurement reference layer 3 along the boundary face between the viscoelasticity measurement reference layer 3 and the specimen 4 to be detected. These strain distributions are supplied from the strain distribution detecting unit 7 to the viscoelasticity distribution calculating unit 8, which is the calculation unit.

[Viscoelasticity Distribution Calculating Unit]

The viscoelasticity distribution calculating unit 8, which is the calculation unit, calculates the modulus-of-elasticity distribution and the coefficient-of-viscosity distribution in the specimen 4 from the saturation value of the strain of the viscoelasticity measurement reference layer 3, the variation with time of the strain distribution in the specimen 4, and the elastic coefficient of the viscoelasticity measurement reference layer 3 in accordance with the above principle.

The viscoelasticity distribution calculating unit 8 may include a microprocessor, a memory, a control circuit controlling the microprocessor and the memory, and a bus circuit for data transfer. Alternatively, the viscoelasticity distribution calculating unit 8 may be installed in a programmable processing circuit, such as a general-purpose personal computer (PC) or a Field Programmable Gate Array (FPGA), in the form of processing software. Accordingly, the processing in the viscoelasticity distribution calculating unit 8 will now be described.

When an ultrasonic wave beam is subjected to the linear scanning for the strain measurement, each position of the ultrasonic wave beam corresponding to each reception beam signal substantially coincides with the direction in which the pressure is applied. Accordingly, the amount of distribution of the viscoelasticity measurement reference layer 3 and the subsequent strain distribution along the depth direction of the specimen 4, which are acquired for every reception beam signal, correspond to the strain on the same vertical column described above with reference to FIG. 3. Consequently, it is possible to advance the processing including the processing in the strain distribution detecting unit 7 for every reception beam signal. When the ultrasonic wave beam is subjected to the sector scanning or other scanning, an array of the amount of strain of the viscoelasticity measurement reference layer 3 and the strain distribution along the depth direction of the specimen 4 is created for every vertical column described above with reference to FIG. 3 by using the geometrical relationship between the position of the ultrasonic wave beam in the scanning and the direction of pressurization. In this case, the array of the strain distributions of the specimen 4 is created by interpolation from the relationship between the position of the ultrasonic wave beam and the position of the vertical column. Although the linear scanning is exemplified here for simplicity, the similar processing can be performed in other beam scanning methods by replacing the array of the amount of strain of the viscoelasticity measurement reference layer 3 and the strain distribution along the depth direction of the specimen 4, corresponding to each reception beam signal, with the vertical data column from the above positional relationship.

A tomographic strain distribution data set at a frame time when a single beam scanning process is performed is acquired in association with the frame reception beam signal data acquired in the beam scanning process. The tomographic strain distribution data set is composed of an array of the amount of strain of the viscoelasticity measurement reference layer 3 and the strain values along the depth direction of the specimen 4, which are acquired from each reception beam signal at the time in association with the single beam scanning. The data set composed of the amount of strain of the viscoelasticity measurement reference layer 3 and the strain values along the depth direction of the specimen 4 for every reception beam signal are called a beam strain distribution data set. In other words, the tomographic strain distribution data set is composed of the multiple beam strain distribution data sets corresponding to the respective reception beam signals at each time. In the tomographic strain distribution data set, each beam strain distribution data set corresponds to the position of the ultrasonic wave beam in the beam scanning. Repeating the beam scanning allows the multiple tomographic strain distribution data sets corresponding to the scanning processes at different points of time to be acquired.

The strain values of the specimen in each beam strain distribution data set in the multiple tomographic strain distribution data sets acquired at different points of time are used to extract the variation with time of the strain of the specimen at each position in the depth direction at the corresponding beam position. The ratio $\tau$ between the Young's modulus and the coefficient of viscosity at each point in the specimen is calculated from the variation with time at each position by using (Equation 7). In order to first differentiate the strain value of the specimen, an increase in the strain of the specimen for every certain time interval from the stepwise pressurization corresponding to each tomographic strain distribution data set is divided by the time interval to calculate an approximate value of the differentiation with respect to time of the strain and $1/\tau$ is calculated from the slope with respect to time of the logarithm of the approximate value of the differentiation with respect to time of the strain according to (Equation 7). $1/\tau$ is desirably calculated from the approximate values of the differentiation of the strain at multiple points of time by the fitting. The intercept with respect to time of the logarithm of the approximate value of the differentiation with respect to time of the strain is simultaneously calculated in the same manner. This processing is performed for all the points in the depth direction at the position of each ultrasonic wave beam and all the positions of the ultrasonic wave beams in the beam scanning to calculate the distribution of the ratio $\tau$ and the intercept at each point on the cross section of the specimen. The approximate value of the differentiation with respect to time of the strain is calculated from the division of the increase in the strain of the specimen by the time interval, high-order central difference, forward difference, backward difference, or the like may be used. Alternatively, (Equation 5') may be directly subjected to the fitting, as described above, to calculate the ratio $\tau$ between the coefficient of viscosity and the Young's modulus and the reference strain coefficient $\sigma_0/E$.

The ratio $\tau$ between the coefficient of viscosity and the Young's modulus and the intercept at each point, which are calculated, is desirably stored in the form of a data array conforming to the tomographic strain distribution data set. The multiple tomographic strain distribution data sets corresponding to the beam scanning at the respective points of time are each composed of the beam strain distribution data sets corresponding to the respective beam positions, and the strain values of the specimen corresponding to the positions in the beam depth direction are arranged in each beam strain distribution data set. In the above structure, the strain values of the specimen arranged in each tomographic strain distribution data set correspond to the points where the strains are measured in the specimen. Accordingly, the strain values of the specimen at the same array position in the multiple tomographic strain distribution data sets at different points of time in the beam scanning are used to calculate the ratio τ and the intercept and to store the values of the ratio τ and the intercept, which are calculated, in a similar data array. As the result, the values of the ratio τ and the intercept at the respective points where the strain of the viscoelasticity measurement reference layer 3 is measured in the manner shown in FIG. 3 are simply associated with the values of the ratio τ and the intercept at the respective points arranged in the depth direction to which the same stress as that at the points where the strain of the viscoelasticity measurement reference layer 3 is measured is applied. However, the data may be stored by another method as long as the above correspondence is achieved. The same applies to the calculation of the ratio τ between the coefficient of viscosity and the Young's modulus and the reference strain coefficient $\sigma_0/E$.

It is possible to calculate the ratio τ between the coefficient of viscosity and the Young's modulus and the intercept with sufficient accuracy by using the pieces of time series strain data at a few to several tens of points of time within the range of the viscoelasticity of the body tissue, which is the specimen, including the case in which the strain data is used in the fitting. Accordingly, it is sufficient to provide a few to several tens of tomographic strain distribution data sets at each time and to provide a few to several tens of pieces of frame reception beam signal data used to create the tomographic strain distribution data sets. It takes only a few seconds to perform the beam scanning for generating the above data. Accordingly, it is sufficient to store the tomographic strain distribution data sets corresponding to several tens of frames in which the distribution of the ratio τ and the intercept is calculated, and the beam scanning to create the data sets may be stopped by the control unit 11 at a time when the beam scanning corresponding to several tens of frames has been finished (when the beam scanning has been performed the number of times corresponding to several tens of frames).

Similarly, also when the ratio τ between the coefficient of viscosity and the Young's modulus and the reference strain coefficient $\sigma_0/E$ are calculated by the direct fitting to the (Equation 5'), it is sufficient for the beam scanning to be performed at the initial points of time in the stepwise pressurization when the fitting is performed.

Then, the beam scanning is restarted at a time when the saturation measurement time is reached. The distribution of the stress of the viscoelasticity measurement reference layer 3 is calculated according to (Equation 6) by using the tomographic strain distribution data sets that are newly created by the strain distribution detecting unit 7 in synchronization with the restart of the beam scanning. In the present embodiment, the stress $\sigma_0$ at each point in the viscoelasticity measurement reference layer 3 is directly calculated by using the known Young's modulus Ec of the viscoelasticity measurement reference layer 3. Then, the calculated stress $\sigma_0$ at each point in the viscoelasticity measurement reference layer 3 is used to calculate the Young's modulus and the coefficient of viscosity from the values of the ratio τ and the intercept at each point in the depth direction of the specimen 4 having the same stress as that at the point in the viscoelasticity measurement reference layer 3. The Young's modulus E at each point in the specimen 4 is first calculated from the stress $\sigma_0$ and the ratio τ by using (Equation 8) given by (Equation 7):

[Math. 13]

$$\text{INTERCEPT} = \ln\left(\frac{\sigma_0}{\tau E}\right) \quad \text{(Equation 8)}$$

When the reference strain coefficient $\sigma_0/E$ is calculated, the Young's modulus E is directly calculated from the stress $\sigma_0$.

[Math. 14]

$$\tau = \frac{\eta}{E} \quad \text{(Equation 9)}$$

Then, the relationship in (Equation 9) is used to calculate the coefficient of viscosity η at each point. The calculation is repeated for the respective points in the specimen 4, which correspond to the respective points in the viscoelasticity measurement reference layer 3, which have the same stress as those of the points in the viscoelasticity measurement reference layer 3, and which are arranged in the depth direction, to calculate the distribution of the Young's modulus (modulus of elasticity) and the distribution of the coefficient of viscosity in the specimen 4.

After the distribution of the Young's modulus (modulus of elasticity) and the distribution of the coefficient of viscosity in the specimen 4 are calculated, the pressurization from the pressure driving unit 12 is stopped by the control unit 11.

The data about the distribution of the modulus of elasticity and the distribution of the coefficient of viscosity, which has been calculated, is supplied to the imaging unit 9. The imaging unit 9 generates a viscoelastic tomographic image in which the viscoelasticity in the specimen 4 is reflected from the multiple pieces of data about the distribution of the modulus of elasticity and the distribution of the coefficient of viscosity.

In the imaging unit 9, the signal processing such as gain adjustment and/or filter processing and the image processing such as edge enhancement and/or image filtering may be performed to generate the viscoelasticity tomographic image, as in the generation of the B-mode tomographic image. In addition, switching between the viscoelasticity tomographic image and the B-mode tomographic image is performed under the display control of the control unit 11 to concurrently display the viscoelasticity image and the B-mode tomographic image in the display unit 10 in a parallel manner or to display the viscoelasticity image and the B-mode tomographic image in the display unit 10 in a superposition manner. Alternatively, in the imaging unit 9, a strain tomographic image may be generated on the basis of the data about the strain distribution in the specimen 4 generated by the strain distribution detecting unit 7 and switching between the strain tomographic image, the viscoelasticity tomographic image, and the B-mode tomographic image may be performed under the display control of the control unit 11 to concurrently display the strain tomographic image, the viscoelasticity image, and the B-mode tomographic image in the display unit 10 in a parallel manner or to display the strain tomographic image, the viscoelasticity image, and the B-mode tomographic image in the display unit 10 in a superposition manner.

In particular, the B-mode tomographic image and the strain tomographic image may be generated by the beam scanning during the stepwise pressurization to allow the variation of the tissue image during the pressurization to be followed.

Although the pair of compression plates 13 is used to hold the specimen 4 in the above description, the above configuration is not limitedly used as long as the specimen 4 and the viscoelasticity measurement reference layer 3 are simultaneously stably held to allow the stepwise pressurization. FIGS. 6A and 6B show other configurations to hold the specimen 4 for the stepwise pressurization.

FIG. 6A shows an exemplary configuration in which the pressure driving unit 12 held by a support post 16 directly applies load on the probe 1. The probe 1 is directly in contact with the viscoelasticity measurement reference layer 3. Protective layers and/or joining layers may be provided for the probe 1 and the viscoelasticity measurement reference layer 3. The pressure driving unit 12 measures a reaction force from the specimen 4 with a load sensor (for example, a load cell) (not shown) to control the load to be applied on the probe 1 by the pressure driving unit 12 on the basis of the measured reaction force. The pressure driving unit 12 is controlled by the pressure driving unit 12 so as to instantaneously apply a certain load on the probe 1 and subsequently keep the certain load. Accordingly, desired stepwise pressurization can be performed to the specimen 4 and the viscoelasticity measurement reference layer 3. Since no compression plate is provided between the probe 1 and the viscoelasticity measurement reference layer 3 in such a configuration, absorption, reflection, and/or scattering of the ultrasonic waves that are transmitted from and input into the probe 1 are suppressed to improve the accuracy of the measurement of the strain using the ultrasonic waves. If a difference in acoustic impedance occurs between the specimen 4 and the viscoelasticity measurement reference layer 3, the joining layers may be provided to suppress the reflection from the boundary between the specimen 4 and the viscoelasticity measurement reference layer 3.

FIG. 6B shows another exemplary configuration in which the belt 17 is used to hold the specimen 4. An end of the belt 17 is fixed to the probe 1 and the binding unit 18 is used to hold the specimen 4. The binding unit 18 is controlled by the control unit 11 so as to measure the tension of the belt 17 to cause the belt 17 to hold the specimen 4 at a constant tension. The binding unit 18 can be controlled so that the tension at which the belt 17 holds the specimen 4 is instantaneously changed to a desired value and the tension is subsequently kept at the desired value to allow the probe 1 to perform the stepwise pressurization to the specimen 4 and the viscoelasticity measurement reference layer 3.

As described above, it is possible to realize the stepwise pressurization by holding the specimen 4 in a manner appropriate for the shape of the specimen 4 and the region in the specimen 4.

Second Embodiment

FIG. 4 is a block diagram showing an example of the configuration of an ultrasonic diagnostic apparatus according to a second embodiment.

In the second embodiment, the probe is scanned to measure three-dimensional distribution of the modulus of elasticity and the coefficient of viscosity of a specimen. The same reference numerals are used in the second embodiment to identify the same components in the first embodiment. A description of such components is omitted herein.

Referring to FIG. 4, the probe scanning unit 15 holds the probe 1 and mechanically scans the probe 1 along one of the compression plates 13 under the control of the control unit 11. The modulus-of-elasticity distribution and the coefficient-of-viscosity distribution on the cross section of the specimen at each position of the probe 1 moved by the probe scanning unit 15 are calculated in the same manner described above in the first embodiment. Tomographic images indicating the modulus-of-elasticity distribution and the coefficient-of-viscosity distribution that are calculated are arranged in a direction in which the probe 1 is scanned by the probe scanning unit 15 to detect the three-dimensional distribution of the modulus-of-elasticity distribution and the coefficient-of-viscosity distribution.

Figure 5A:
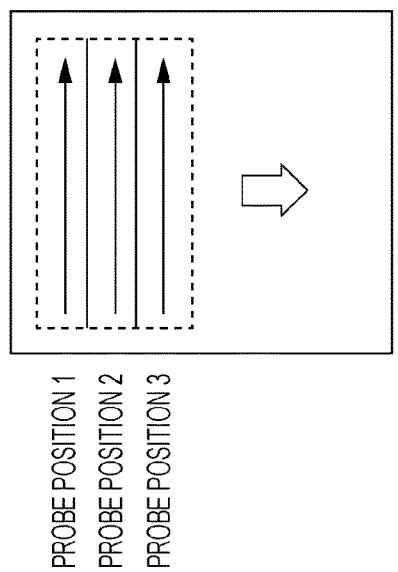
FIG. 5A shows an example of how a probe scanning unit scans a probe on a compression plate and also shows beam scanning by the probe at each probe position.
Figure 5B:
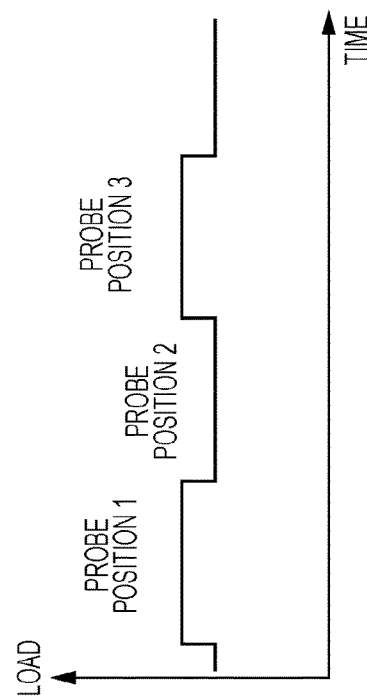
FIG. 5B is an exemplary graph showing the magnitude of a load applied on a specimen and a viscoelasticity measurement reference layer at each probe position.
Figure 5C:
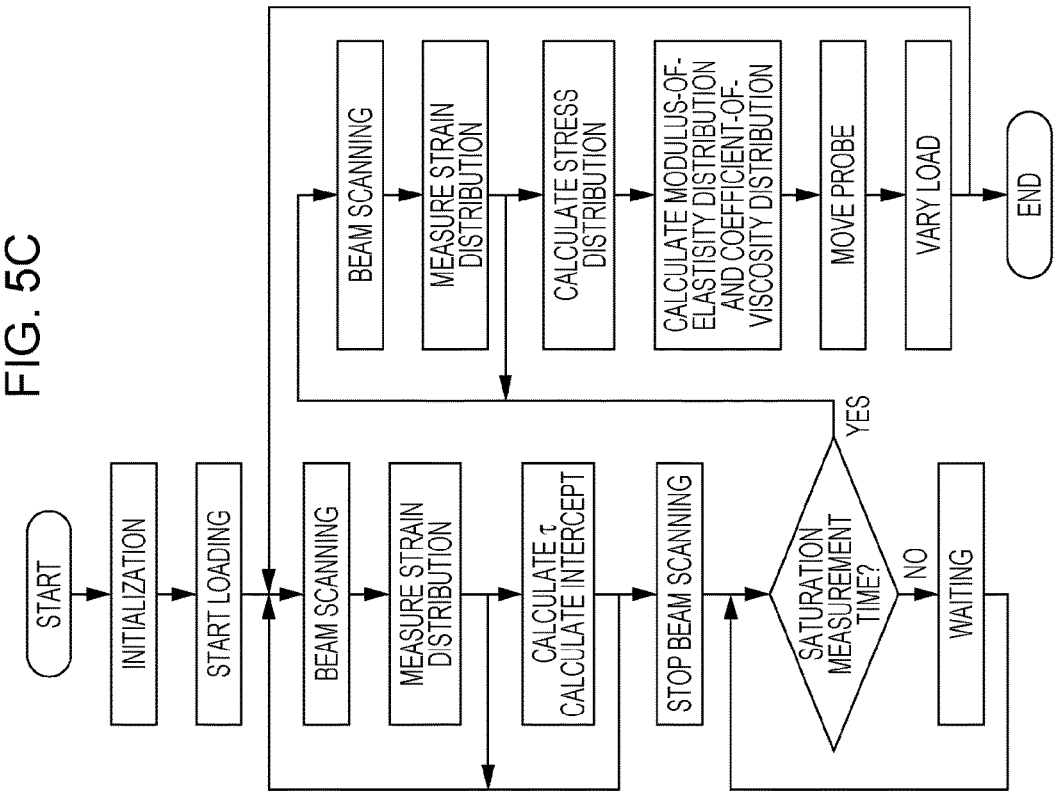
FIG. 5C is a flow chart showing an exemplary operational process in the second embodiment.

FIGS. 5A, 5B, and 5C show operations in the second embodiment. The operations in the second embodiment will now be described with reference to FIGS. 5A, 5B, and 5C.

FIG. 5A shows an example of how the probe scanning unit 15 scans the probe 1 on the compression plate 13 and also shows the beam scanning by the probe at each probe position in conjunction with the scanning of the probe 1. The scanning with the ultrasonic wave beams is performed at a probe position 1, a probe position 2, a probe position 3, . . . in the manner described above in the first embodiment in conjunction with the scanning of the probe to calculate a two-dimensional distribution image of the modulus of elasticity and the coefficient of viscosity on a cross section of the beam scanning.

FIG. 5B is an exemplary graph showing the magnitude of the load applied on the specimen 4 and the viscoelasticity measurement reference layer 3 by the pressure driving unit 12 at each probe position. After the probe 1 is moved to each probe position by the probe scanning unit 15, the load between the two compression plates 13 with the specimen 4 sandwiched therebetween is controlled by using a measured load value from the load sensor (not shown) under the control of the control unit 11 to instantaneously vary the load to a certain value. Then, the certain load value is held for a certain time period to perform the stepwise pressurization. Different loads are applied at different probe positions in the second embodiment. The same load is desirably applied at odd-number positions including the probe position 1, the probe position 3, . . . and the same load that is different from that at the odd-number positions is desirably applied at even-number positions including the probe position 2, a probe position 4, . . . . A load substantially close to zero is more desirably applied at either of the odd-number positions and the even-number positions as long as the specimen 4 is stably held by the compression plates 13. The constant load applied on each probe position by the pressure driving unit 12 is kept for a time period longer than the saturation measurement time.

Also when the constant load is applied on the probe 1 with the pressure driving unit 12, the pressure (stress) applied from the compression plates 13 on the specimen 4 exhibits different distributions at different positions depending on the shape of the specimen 4 and the internal hardness thereof. However, the stepwise pressurization is performed with respect to time at each point on the face on which the specimen 4 is in contact with the compression plate 13 by the above method of controlling the load. Accordingly, the stepwise pressurization is performed on each point in the specimen 4 and the viscoelasticity measurement reference layer 3.

FIG. 5C is a flow chart showing an exemplary operational process in the second embodiment. Referring to FIG. 5C, upon start of the operation, the probe 1 is set at a first probe position. A load of a first load value is applied on the compression plate 13 from the pressure driving unit 12. The stepwise pressurization is performed to each point in the specimen 4 and the viscoelasticity measurement reference layer 3 with this load. The beam scanning with the ultrasonic waves is started to measure the strain distribution in the specimen 4 on the cross section at the first probe position by using the echo signal of the ultrasonic wave beam transmitted from and input into the probe 1. The beam scanning is repeated to calculate the ratio τ between the coefficient of viscosity and the Young's modulus and the intercept at each point in the specimen 4 from the variation in the strain distribution in the specimen 4. However, the intercept resulting from correction of the initial strain of the specimen 4 is used here. Then, the beam scanning is stopped and enters a waiting mode until the saturation measurement time. The beam scanning is restarted at the saturation measurement time to measure the strain distribution of the viscoelasticity measurement reference layer 3 and calculate the stress at each point of the viscoelasticity measurement reference layer 3 in order to calculate the values of the modulus of elasticity and the coefficient of viscosity at each point in the specimen 4 by using the calculated stress and the ratio τ between the coefficient of viscosity and the Young's modulus and the intercept at each point in the specimen 4.

Then, the probe 1 is moved to a second probe position and the value of the load applied on the compression plate 13 from the pressure driving unit 12 is changed to a second load value. The beam scanning is simultaneously performed to measure the strain distribution in the specimen 4, to calculate the ratio τ between the coefficient of viscosity and the Young's modulus and the intercept from the variation in the strain distribution, and to calculate the stress distribution of the viscoelasticity measurement reference layer 3 at the saturation measurement time in order to calculate the values of the modulus of elasticity and the coefficient of viscosity at each point in the specimen 4. Then, the probe 1 is moved to a third probe position and the value of the load applied on the compression plate 13 from the pressure driving unit 12 is changed (returned) to the first load value to repeat the above operation. The operational process is terminated at a time when the position of the probe 1 reaches a final scanning position and the series of measurement is completed.

The load value after the movement of the probe 1 is desirably varied in the manner shown in FIG. 5B, in which two load values alternately appear. In addition, the lower load value is desirably set to a value substantially equal to zero. In the present embodiment, the load on the compression plate 13 from the pressure driving unit 12 is varied to vary the pressure applied on each point in the specimen 4 and of the viscoelasticity measurement reference layer 3 each time the probe 1 is moved. However, since the load on the compression plate 13 from the pressure driving unit 12 is kept at a constant value by the control unit 11 while the strain on the cross section is being measured by the beam scanning at each probe position, the stepwise pressurization is performed to the specimen 4 and the viscoelasticity measurement reference layer 3. Although the initial strain caused by the previous pressure occurs in the specimen 4 at the start of the stepwise pressurization, that is, at a moment when the value of pressure is varied in the present embodiment, the intercept represented in the following manner can be corrected against the initial strain or (Equation 5) can be subjected the fitting to calculate the modulus of elasticity and the coefficient of viscosity at each point in the specimen in the above manner.

$$\ln\left(\frac{\sigma_0}{\tau E} - \frac{\varepsilon^{(0)}}{\tau}\right)$$ [Math. 15]

In particular, when the value of the load to be varied depending on the position of the probe is set to a value between a certain finite value and a value substantially equal to zero, as described above, the stress occurring when the load of a value substantially equal to zero is applied is substantially equal to zero. The value of the strain of the viscoelasticity measurement reference layer 3 at this time is close to zero and is substantially equal to zero after the saturation measurement time. Since the value of the strain in the specimen 4 is also close to zero with time, the initial strain in the specimen 4 at the subsequent probe position in the scanning of the probe may be considered to be zero as long as the saturation measurement time is set to a long value. Even when the value of the strain in the specimen 4 does not reach zero at the saturation measurement time, the value of the strain in the specimen 4 is varied to zero. As described above, the value of the load applied with the pressure driving unit 12 can be alternately varied between two high and low values, as shown in FIG. 5B, to prevent the initial strain at the start of the stepwise pressurization from being accumulated.

In the measurement at each probe position by the scanning of the probe described above, the calculation of the ratio τ between the coefficient of viscosity and the Young's modulus and the intercept at each point in the specimen 4 is performed continuously with the calculation of the stress at each point from the strain distribution of the viscoelasticity measurement reference layer 3. However, in the scanning of the probe, the ratio τ between the coefficient of viscosity and the Young's modulus and the intercept may be first calculated at each point in the specimen 4 at each probe position, the scanning of the probe may be continued while the calculated ratio τ and the intercept are being stored in the memory, and the scanning of the probe may be performed again to detect the stress distribution from the strain of the viscoelasticity measurement reference layer 3. In other words, the calculation of the ratio τ between the coefficient of viscosity and the Young's modulus and the intercept and the calculation of the stress distribution are performed in separate series of scanning of the probe. In this case, there is no need to wait for the saturation measurement time after the value of the load with the pressure driving unit 12 is varied at each probe position and the ratio τ between the coefficient of viscosity and the Young's modulus and intercept are calculated. After the ratio τ and the intercept are calculated from the variation with time of the strain distribution in the specimen 4, the probe is immediately moved to measure the strain at the subsequent probe position. After the scanning of the probe is performed to a certain area and the saturation measurement time elapsed, the scanning of the probe is performed again to calculate the stress at each point from the strain distribution of the viscoelasticity measurement reference layer 3 at each probe position and store the calculated stress in the memory. After the re-scanning of the probe is terminated, the ratio τ, the intercept, and the stress at each point, which are stored in the memory, are used to calculate the modulus of elasticity and the coefficient of viscosity at each point in the entire area of the scanning of the probe.

When the above operation is performed, it is not necessary to vary the value of the load with the pressure driving unit 12 in the re-scanning of the probe. If the saturation measurement time in the final stepwise pressurization is elapsed at the time when the re-scanning of the probe is started, the strain at each point of the viscoelasticity measurement reference layer 3 is proportional to the stress according to (Equation 6). Accordingly, it is sufficient for the waiting for the saturation measurement time to be performed once between the first scanning of the probe in which the ratio τ and the intercept are calculated and the re-scanning of the probe in which the stress is calculated. Consequently, the above operation has the advantage of reducing the entire measurement time despite the fact that the scanning is performed twice.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-118095, filed May 26, 2011, which is hereby incorporated by reference herein in its entirety.

The invention claimed is:

1. A specimen information acquisition apparatus that transmits elastic waves to a specimen and receives the elastic waves reflected in the specimen to acquire information in the specimen, the specimen information acquisition apparatus comprising:
 a probe including a transducer that converts the received elastic waves into an electrical signal;
 a measurement unit that measures a strain in the specimen and a strain of a reference layer provided between the transducer and the specimen when pressure is applied on the specimen and the reference layer by using the electrical signal, the reference layer having a known modulus of elasticity;
 a pressure applying unit that applies pressure on the specimen via the reference layer in a stepwise manner with respect to time by pressing the reference layer against the specimen; and
 a calculation unit that calculates a coefficient of viscosity and a modulus of elasticity of the specimen by using the modulus of elasticity of the reference layer, a variation in the strain in the specimen, and a saturation value of the strain of the reference layer after the pressure applying unit applies the pressure in the stepwise manner.

2. The specimen information acquisition apparatus according to claim 1,
 wherein the pressure applying unit includes a compression member,
 wherein the reference layer is positioned on a side of the compression member opposing the specimen so as to be arranged between the specimen and the compression member, and
 wherein the transducer is positioned on a side opposite to the side of the compression member opposing the specimen so as to transmit and receive the elastic waves to and from the specimen via the compression member and the reference layer.

3. The specimen information acquisition apparatus according to claim 2, further comprising:
 a scanner that moves the probe along the compression member and relative to the specimen,
 wherein the pressure applying unit controls the pressure so that the compression member performs stepwise pressurization in which different pressures are applied on the specimen and the reference layer at each position of the transducer to be scanned,
 wherein the measurement unit measures strain distribution in the specimen and strain distribution of the reference layer on the basis of the stepwise pressurization, and
 wherein the calculation unit calculates coefficient-of-viscosity distribution of the specimen by using the modulus of elasticity of the reference layer, the strain distribution in the specimen, and distribution of the saturation value of the strain of the reference layer.

4. The specimen information acquisition apparatus according to claim 1,
 wherein the pressure applying unit includes a tension band that holds the specimen, and
 wherein the pressure applying unit controls a tension of the tension band to control the pressure to be applied on the specimen and the reference layer.

5. The specimen information acquisition apparatus according to claim 1, wherein the reference layer has a thickness of 0.1 mm to 50 mm.

6. The specimen information acquisition apparatus according to claim 5, wherein the reference layer has a thickness of 1 mm to 10 mm.

7. The specimen information acquisition apparatus according to claim 1, further comprising a processor that obtains a tomographic image of the specimen based on the elastic waves reflected in the specimen.

8. The specimen information acquisition apparatus according to claim 7, wherein the processor causes a display to display the tomographic image and an image of viscoelasticity of the specimen.

9. A specimen information acquisition method comprising:
 receiving, using a probe including a transducer, elastic waves transmitted to and reflected in the specimen via a reference layer having a known modulus of elasticity;
 converting, using the transducer, the received elastic waves into an electrical signal;
 measuring, using a measurement unit, a strain in the specimen and a strain of the reference layer provided between the transducer and the specimen when pressure is applied on the specimen and the reference layer by using the electrical signal;
 applying pressure on the specimen via the reference layer in a stepwise manner with respect to time by pressing the reference layer against the specimen; and
 calculating, using a processor, a coefficient of viscosity and a modulus of elasticity of the specimen by using the modulus of elasticity of the reference layer, a variation in the strain in the specimen, and a saturation value of the strain of the reference layer, after the pressure is applied in the stepwise manner.

10. The specimen information acquisition method according to claim 9, further comprising:
 positioning the reference layer on a side of the compression member opposing the specimen so as to be arranged between the specimen and the compression member,
 wherein the conversion transducer is positioned on a side opposite to the side of the compression member opposing the specimen so as to transmit and receive the elastic waves to and from the specimen via the compression member and the reference layer.

11. The specimen information acquisition method according to claim 10, further comprising:

moving the probe along the compression member and relative to the specimen, controlling the pressure so that the compression member performs stepwise pressurization in which different pressures are applied on the specimen and the reference layer at each position of the transducer to be scanned, measuring strain distribution in the specimen and strain distribution of the reference layer on the basis of the stepwise pressurization, and calculating coefficient-of-viscosity distribution of the specimen by using the modulus of elasticity of the reference layer, the strain distribution in the specimen, and distribution of the saturation value of the strain of the reference layer.

12. The specimen information acquisition method according to claim 9, further comprising obtaining a tomographic image of the specimen based on the elastic waves reflected in the specimen.

13. The specimen information acquisition method according to claim 12, further comprising causing a display to display the tomographic image and an image of viscoelasticity of the specimen.

\* \* \* \* \*